US006926704B2

(12) United States Patent
Andersson et al.

(10) Patent No.: US 6,926,704 B2
(45) Date of Patent: Aug. 9, 2005

(54) ABSORBENT DISPOSABLE ARTICLE

(75) Inventors: Mikael Andersson, Göteborg (SE);
Ken Olsson, Västra Frölunda (SE);
Anna-Karin Storm, Göteborg (SE)

(73) Assignee: SCA Hygiene Products AB,
Gothenburg (SE)

( * ) Notice: Subject to any disclaimer, the term of this patent is extended or adjusted under 35 U.S.C. 154(b) by 307 days.

(21) Appl. No.: 10/178,529

(22) Filed: Jun. 25, 2002

(65) Prior Publication Data

US 2003/0014030 A1 Jan. 16, 2003

Related U.S. Application Data

(60) Provisional application No. 60/300,064, filed on Jun. 25, 2001.

(51) Int. Cl.[7] ............................................... A61F 13/15
(52) U.S. Cl. .................................. 604/385.13; 604/389
(58) Field of Search ....................... 604/385.13, 385.19, 604/389

(56) References Cited

U.S. PATENT DOCUMENTS 4,911,702 A * 3/1990 O'Leary et al. ............ 604/389
5,575,784 A 11/1996 Ames-Ooten et al.
6,475,205 B2 * 11/2002 Shimada et al. ....... 604/385.13

FOREIGN PATENT DOCUMENTS

| EP | 0 623 330 A2 | 11/1994 |
| EP | 0 732 094 A2 | 9/1996 |
| EP | 0 826 352 A2 | 3/1998 |
| EP | 0 951 885 A2 | 10/1999 |
| WO | WO 01/13842 A1 | 3/2001 |

* cited by examiner

Primary Examiner—Larry I. Schwartz
Assistant Examiner—C. Lynne Anderson
(74) Attorney, Agent, or Firm—Burns, Doane, Swecker & Mathis, L.L.P.

(57) ABSTRACT

An absorbent disposable article, such as nappy pants, has a T-shaped tape attached on the outside of the article with such adhesion that the tape withstands a load of at least 25 N in the tape flap without the tape coming away from the outer layer. The tape flap is arranged in a parked state during use and can also be used to seal the article into a closed, folded package after use. When the tape flap has been freed from its parked state, the tape flap forms a stem portion of a T with the two cross-legs of the T permanently attached to the outer layer, so the tensile forces in the tape flap are taken up by the two legs. The outer layer includes a non-woven laminate, with at least one outer ply of spunbond and an inner ply of at least one meltblown.

14 Claims, 3 Drawing Sheets

ABSORBENT DISPOSABLE ARTICLE

CROSS REFERENCE TO RELATED APPLICATIONS

The present application claims the priority under 35 U.S.C. § 119 of U.S. Application No. 60/300,064, filed in the United States on Jun. 25, 2001, the entire contents of which are hereby incorporated by reference.

BACKGROUND OF THE INVENTION

1. Field of the Invention

The present invention relates to an absorbent disposable article, such as nappy pants, a sanitary towel in the form of briefs or the like, which comprises an inner layer which faces the wearer during use of the article, an outer layer and an absorbent element arranged between the outer and inner layers. The article has a crotch portion and, located on both sides of the latter, waist portions which surround the waist of the wearer during use of the article. A tape is permanently attached by a portion on the outside of said outer layer, said tape having a tape flap which is arranged in a parked state during use of the article and which can be brought from its parked state into a state of use in order, after use of the article and after folding or rolling together of the latter to form a package, to be usable for closing the package formed.

2. Background Art

After using sanitary disposable articles, such as nappies and sanitary towels, it is desirable, principally for hygienic reasons but also for aesthetic reasons, to be capable of enclosing the used article in a package in order to prevent feces, urine or menstrual fluid taken up in the article from leaking out or causing soiling. When a wearer wishes to replace a used article with a new one, it is often not easy to dispose of the used article in a hygienically satisfactory manner if the wearer is not at home. One does not of course always have a refuse bag for used sanitary articles to hand and, if there is a waste bin or the like, it is not satisfactory openly to discard used sanitary articles therein. Hygienic bags for used sanitary towels are included with packs of sanitary towels, but this is not the case as far as the sale of nappies for infants is concerned, and parents and others who are responsible for a toddler must always be mindful of having a refuse bag at hand.

In the use of a certain type of nappy for infants with tape, which for a time was the predominant type of nappy for infants, it was easy to solve the abovementioned problem of handling used nappies by means of the tape which is used for attaching the nappy to the infant. In order for this to function, it is a prerequisite that the tape on a nappy fitted to an infant can be freed without the tape flap taking material along with it on its attachment surface, which material would make it impossible to use the tape again. A nappy with usable attachment tape can be folded or rolled together to form a suitable package which is closed by means of the tape.

In the use of what are known as hook-and-loop connections which are now common, this type of connection often does not function for closing a used nappy to form a package. In order for it to work, it is a prerequisite that the hook-and-loop hooks can be attached to the outer layer of the nappy, which is frequently not the case.

The use of nappy pants has become increasingly common and in these there is of course no tape or the like at all which can be used for closing a used article which has been folded or rolled to form a package for disposal. It has therefore become usual to provide nappies with hook-and-loop connections and also nappy pants with a special tape which is intended to be used solely for closing folded or rolled-together used nappies or nappy pants. These tapes are positioned on the outside of the article and in the waist portion on the front or rear side of the nappy or nappy pants. The folding together or rolling together of a used article is effected from that end portion of the article which is not provided with the tape, after which the tape flap is raised from its parked position and is attached to the folded or rolled-together portion.

The use of tape for closing a folded-together or rolled-together used sanitary article, such as nappy pants, is associated with a great many problems. The adhesion of the tape flap to the outside of the article is of course dependent on the choice of outer material for the article. If the outer layer is made of plastic, a commercially available nappy tape will attach without problems. However, it has been found that consumers prefer sanitary disposable articles, such as nappy pants, which have a textile-like outside, and plastic is then not an alternative, but use is made of various types of non-woven fabrics which can be constituted by one layer of non-woven or consist of a laminate of the same type or different types of non-woven. Said non-woven fabrics are in turn usually laminated with a liquidtight plastic film.

The tape for closing folded-together or rolled-together nappy pants can consist of one part in the form of a hook-and-loop connection while the other part consists of either the outside of the article or a special receiving zone which is arranged in a suitable place on the outside of the article in order to interact with the tape. However, such solutions are relatively expensive and do not solve the particular problems which embodiments of the present invention solve, namely that the permanent connection of the tape to the outer layer of the article is sufficiently strong.

A problem which has certainly been taken into account but not solved in a satisfactory manner in the manufacture of previously known sanitary disposable articles with special tape for closing used articles to form a package for disposal is that, for safety reasons, the tape has to be strongly anchored on the outside of the article. There is a risk that an infant will work the tape loose and swallow it.

The object of the present invention is to produce a construction which affords such permanent anchoring of the tape so an infant will not be able to work the tape loose from the remainder of the article by pulling the tape flap.

As these products are disposable articles in a fiercely competitive marketplace, the solution must be produced at the lowest possible price. At the same time, other requirements relating to the outer layer of the disposable article have to be satisfied, that is to say it is to be so hardwearing that there is no risk of it breaking during normal use and handling, and at the same time the material is to feel soft and pleasant to the wearer and to afford the appearance and sensation of textile. All these requirements result in it being difficult to find a satisfactory solution.

All known commercially available sanitary disposable articles with special tape for closing used articles folded or rolled together to form a package have been reviewed in order to determine whether or not the tape is fixed adequately safely. In this connection, it was established that not one known article we examined was satisfactory from the point of view of safety. An infant would be able to pull the tape loose and swallow it. The degree of adhesion of the tape depends on the adhesive capacity of the tape, the choice of outer layer on the disposable article and the construction of the tape. In the articles examined, the resistance to pulling in the longitudinal direction of the tape attachment surface is adequate, that is to say the tape performs its intended function well. On the other hand, it is easy to free the tape if the free tape flap end is pulled in the direction towards the opposite, anchored end of the tape, that is to say the tape is rolled off bit by bit.

From EP 0 826 352 A2, a construction of the tape is known, which makes this type of pulling-off, that is to say pulling off bit by bit, impossible. The tape according to said publication has two attachment legs permanently anchored to the outer layer, and the free tape flap end has its attachment where these attachment legs meet and is connected to each of these. If, therefore, pulling takes place in the direction towards the end of one of the permanently anchored attachment legs, no peeling-off of this leg takes place because the force will be taken up in the longitudinal direction of the other leg permanently connected to the outer layer. A tape attachment can therefore not be freed as easily by an infant as the constructions available on the market. The stresses on an attachment according to said publication are greatest when the tape flap is pulled at right angles out from the plane of the outer layer. EP 0 826 352 A2 provides no indication of how the outer layer is to be designed or how great a stress the tape will withstand before it comes away. In EP 0 826 352, it is stated that the outer layer consists of a plastic film, which means that the problems in the form of low tape adhesion associated with the use of a non-woven fabric as the outer layer are not addressed.

SUMMARY

According to an embodiment of the invention, an absorbent article of the type mentioned in the introduction is characterized in that the tape is designed so that it is essentially T-shaped in longitudinal section when the tape flap has been freed from its parked state and raised into an extended state projecting straight out from the outer layer, the tape flap forming a stem portion of said T while the two cross-legs of said T constitute the portion permanently attached to the outer layer, as a result of which tensile forces in the tape flap are taken up either by the two legs or in the longitudinal direction by one leg, in that the outer layer consists of a laminate of non-woven fabric, which laminate contains at least one outer ply of spunbond non-woven and an inner ply of at least one meltblown non-woven, and in that the tape is permanently attached to the outer layer with such adhesion that the tape withstands a load of at least 25 N in said tape flap without the tape coming away from the outer layer.

Research has shown that an infant is incapable of exerting a tensile force as great as 25 N. This and other desirable criteria, such as textile appearance and textile feel and also low cost, have been achieved by an article having said features.

According to one embodiment, the two legs of the tape and the movable tape flap have a width of at most 30 mm, suitably at most 20 mm. Restricting the width to this value is suitable from the point of view of cost and also for environmental reasons. Material savings in disposable products are of course especially important for environmental reasons.

According to another illustrative embodiment, the outer layer consists of an SSMMS laminate. It has been found that this laminate affords a very high adhesive power at the same time as it is suitable for the purpose of saving material.

According to another illustrative embodiment, the tape means is attached to the outer layer with such adhesion that the tape flap withstands a load of at least 30 N without the tape coming away from the outer layer.

Further embodiments emerge from the other patent claims.

BRIEF DESCRIPTION OF THE DRAWINGS

The invention will be described in greater detail below with reference to illustrative embodiments shown in the accompanying drawings.

DETAILED DESCRIPTION OF PREFERRED EMBODIMENTS

Figure 1:
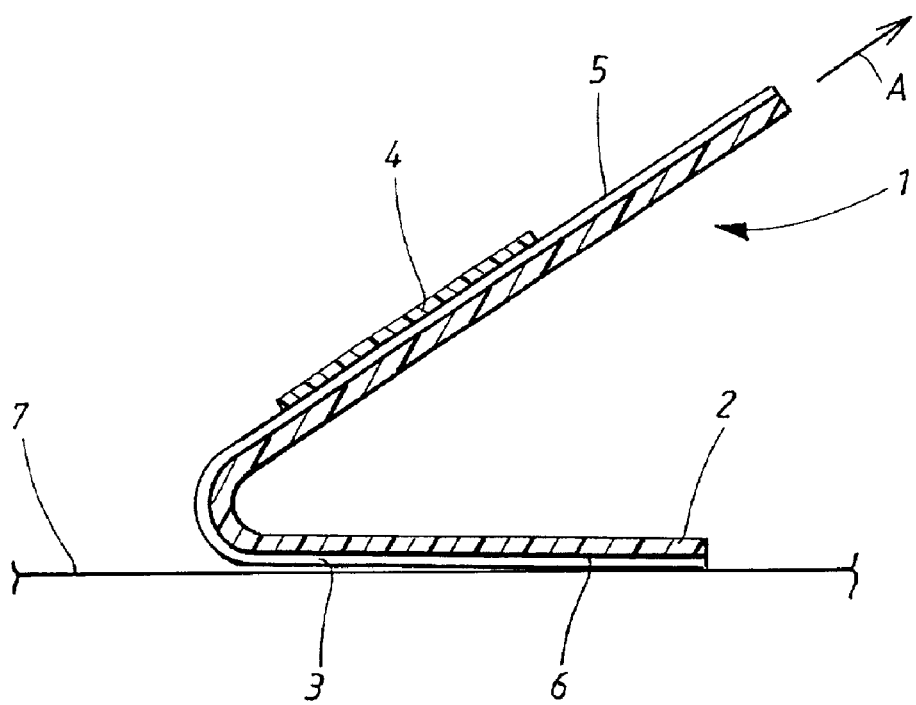
FIG. 1 shows diagrammatically the anchoring of a previously known tape for closing a package consisting of a used absorbent product.

FIG. 1 shows a tape 1 of the type used in commercially available absorbent disposable products, which is intended, after use and folding-together of the product, to close the product in this folded-together state. The tape 1 consists of a support 2 and an adhesive 3 arranged thereon. The tape has a layer 4 which is attached to the adhesive 3 and the outside of which is treated with release agent in order that the free end portion 5 provided with adhesive will be capable in a parked state of being attached detachably to said layer 4. The tape has an end portion 6 provided with adhesive, which is intended to be permanently arranged on the outside 7 of the absorbent product. FIG. 1 shows what would occur if, for example, an infant were to take hold of the free end of the tape 1 and pull in the direction of the arrow A. The portion 6 intended for permanent attachment would then be peeled off bit by bit from the base 7. This is illustrated in FIG. 1 by a part of the portion provided with adhesive having been peeled off from the base to some extent.

Figure 2:
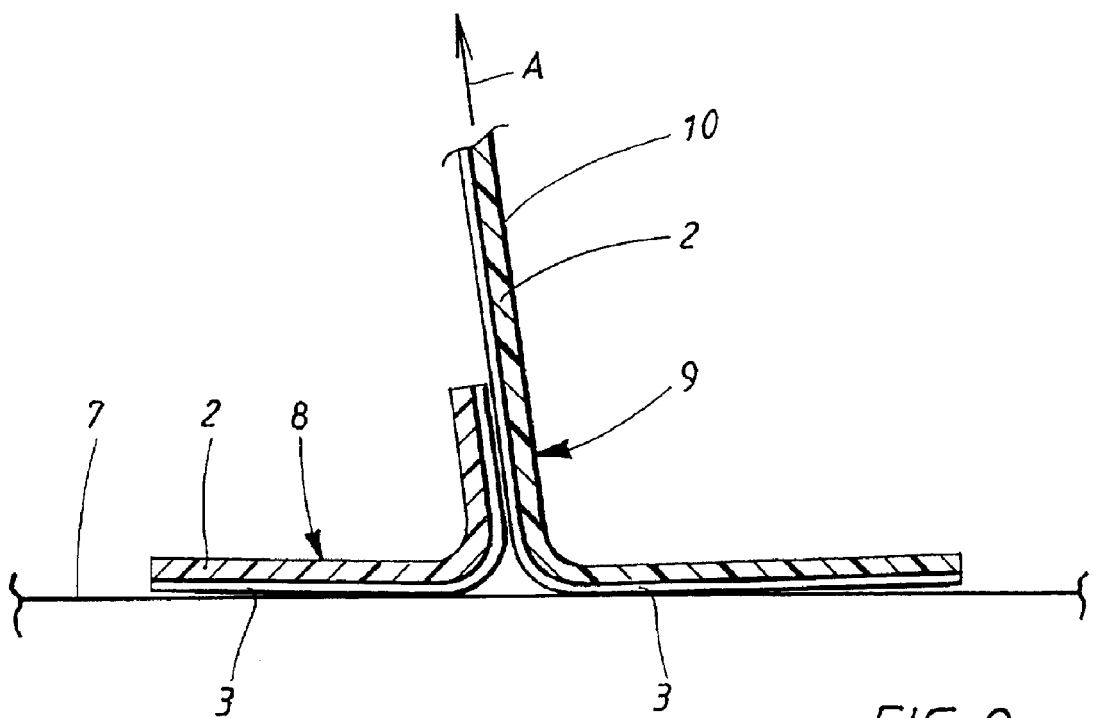
FIG. 2 shows diagrammatically the anchoring principle of a tape forming part of the product according to an embodiment of the present invention.

FIG. 2 illustrates a tape which, compared with the construction according to FIG. 1, is more suitably designed and is of a type which is intended to be used in an absorbent product according to an embodiment of the present invention. The tape consists of two tape portions, a shorter tape portion 8 and a longer tape portion 9, which consist of a support 2 and an adhesive 3. As can be seen from FIG. 2, the two tape portions 8 and 9 are interconnected along part of their extent, adhesive to adhesive. As a result, this connection is very strong. The long tape portion 9 has a free end 10, only a part of which is shown in the drawing. This free end is intended to constitute the tape flap. The tape portions 8 and 9 form two legs, by means of which the tape is attached to the base 7, that is to say the outside of an absorbent article. The anchoring of the tape according to FIG. 2 is much stronger than the anchoring according to FIG. 1. The tape according to FIG. 2 cannot be peeled off easily bit by bit as shown in FIG. 1. The most critical case of loading for the anchoring according to FIG. 2 is when the free tape flap is pulled at right angles to the base 7, that is to say as illustrated by the arrow A in FIG. 2. Even in this case, however, the anchoring is very good compared with a construction according to FIG. 1.

Figure 3:
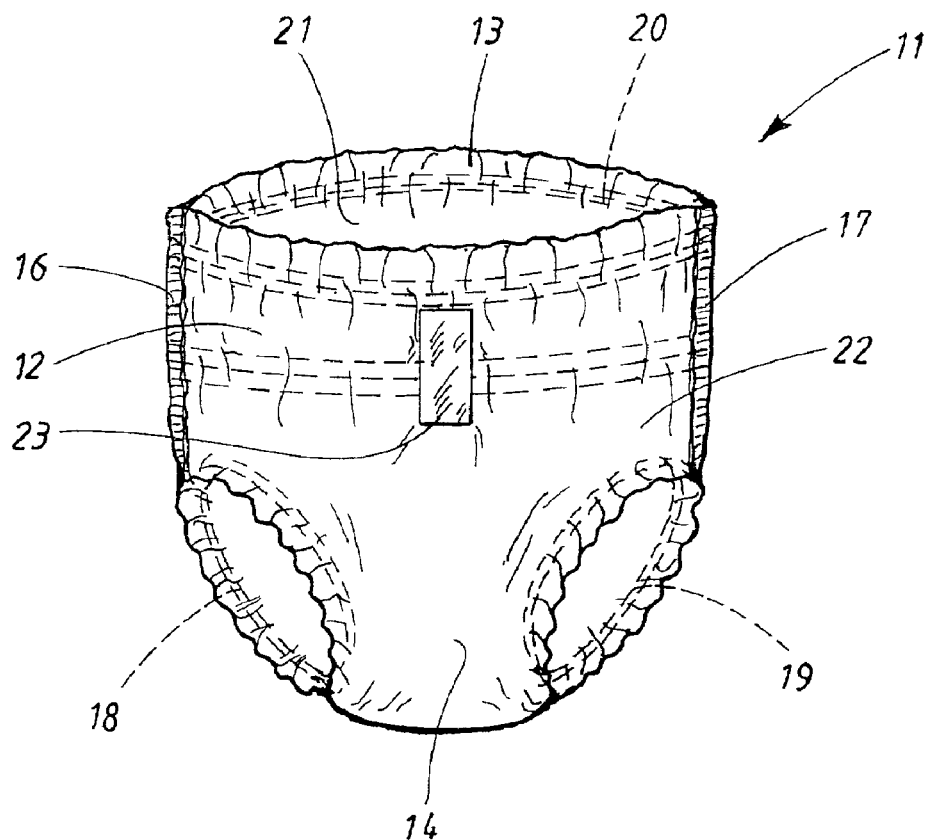
FIG. 3 shows in perspective an absorbent article according to an embodiment of the invention in the form of nappy pants with a tape intended for closing rolled-together or folded-together nappy pants after use.

FIG. 3 shows nappy pants 11 which consist of two waist portions 12, 13 and also an intermediate crotch portion 14. The waist portions 12, 13 are permanently connected along the edge portions 16, 17. The nappy pants have leg openings with leg elastic 18, 19 arranged around these. The nappy pants are also provided with waist elastic 20 for sealing contact around the waist of the wearer. The nappy pants have an inner layer 21 in contact with the wearer and an outer layer 22 and also have an absorbent element (not shown) arranged between said layers.

A tape 23 is arranged in the middle of the front waist portion 12. The tape is of a construction which is described in greater detail below with reference to FIG. 4 and is shown in FIG. 3 in a parked state, from which a tape flap can be pulled out in the upward direction over and past the front waist portion 12 in order to be capable, after the used nappy pants have been folded together or rolled together, of closing the package formed by connecting the front waist portion to a portion of the outer layer on the opposite side of the waist opening.

In the embodiment shown, the tape has been arranged on the front waist portion 12 for the sake of clarity. However, it is more suitable to position the tape permanently on the rear waist portion because it is more difficult for an infant to take hold of the tape and play with it if the tape is permanently arranged at the rear of the nappy pants.

Figure 4:
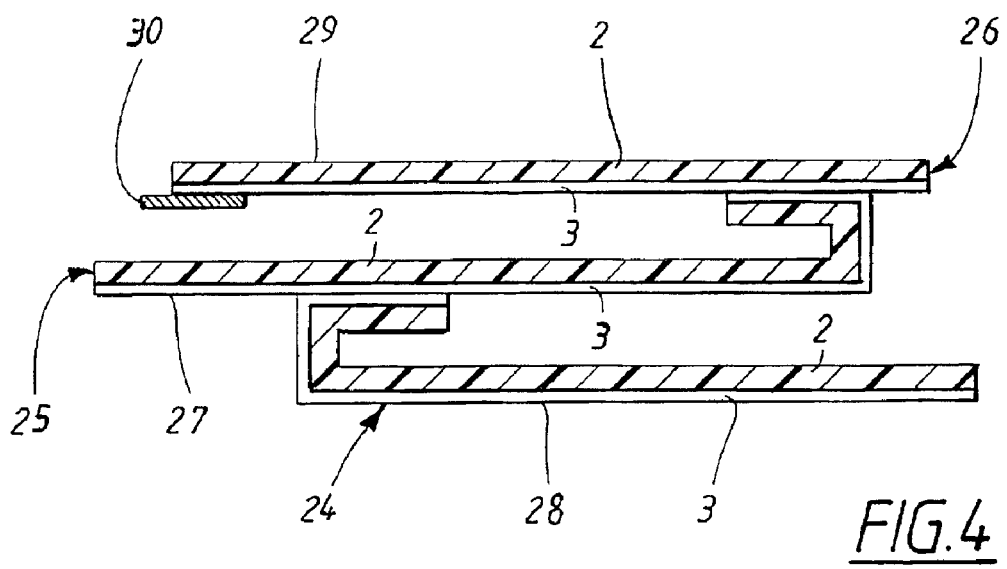
FIG. 4 shows a longitudinal section of an embodiment of a tape forming part of a product according to an embodiment of the invention.

FIG. 4 shows in detail an example of a tape of the type shown in FIG. 3. Here, the tape is constructed from three tape portions 24, 25 and 26. As in the tape described above, the different tape portions consist of a support 2 and an adhesive 3. The portions 27 and 28 form the two legs which are intended to be connected permanently to the outer layer 22 of the nappy pants in FIG. 3, that is to say to be fixed permanently to the base 7 in the same manner as the legs in the basic design shown in FIG. 2. The remaining part of the tape portion 25 and the tape portion 26 together form the free tape flap 29 which is shown in its parked state in FIG. 4. In this state, the tape is as a whole Z-folded, and the outer tape portion 26 is attached by its side provided with adhesive to the support 2 on the tape portion 25, while that part of the tape flap 29 formed by the tape portion 25 is attached detachably to the support 2 on the tape portion 24. In order to facilitate freeing of the tape flap from its parked state, a strip 30 has been arranged on the free end portion of the tape flap.

Figure 5:
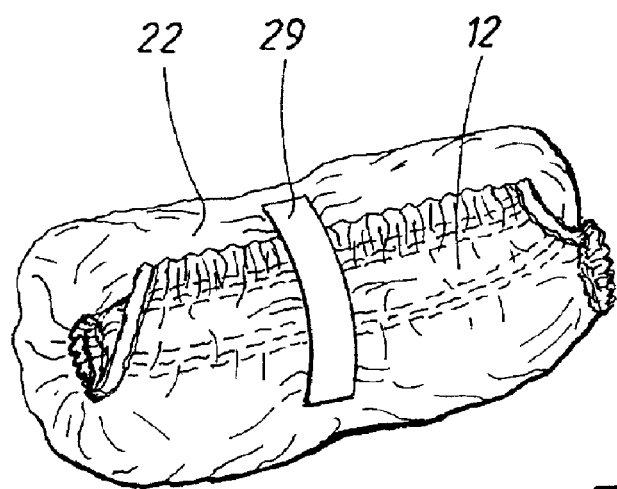
FIG. 5 shows the nappy pants shown in FIG. 3 after use and in the folded-together state.

FIG. 5 shows how folded-together used nappy pants have been secured in the folded-together state by means of the tape flap 29 which has been raised from its parked state and extended from the front waist portion of the nappy pants over the waist opening and attached to the outer layer 22 in a place on the opposite side of the waist opening of the nappy pants.

Research has shown that infants are incapable of exerting tensile forces exceeding the order of 25 N. A tape according to an embodiment of the present invention is therefore anchored to the outer layer of the nappy pants with such adhesion that the tape can take up a load in the tape flap of at least 25 N irrespective of the direction in which the tensile force is exerted.

Figure 6:
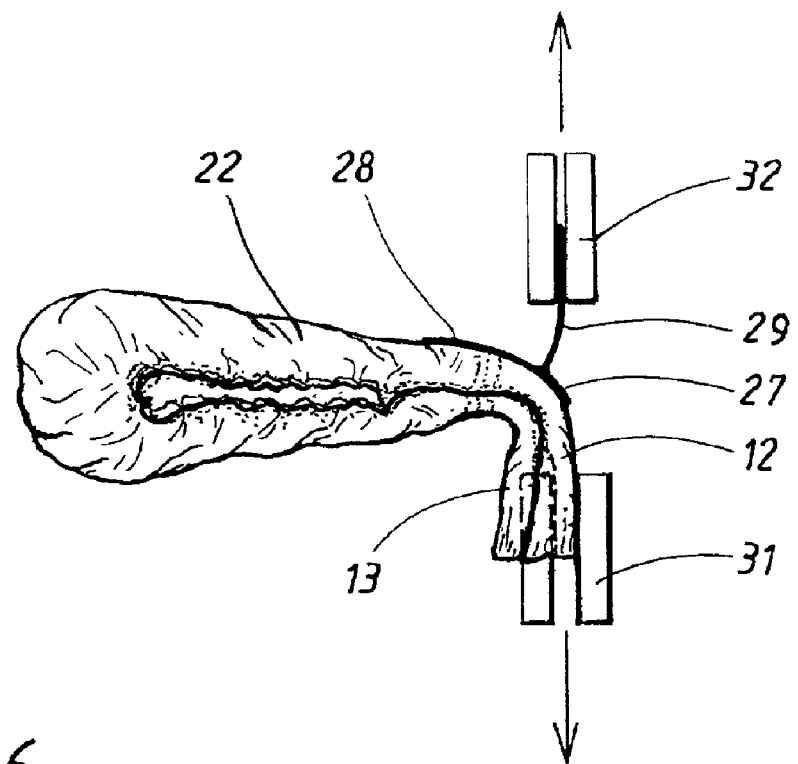
FIG. 6 shows diagrammatically the method of measuring the force necessary to pull a tape from its anchoring.

FIG. 6 illustrates the method of measuring the load on the tape. The measurements are performed in a tensile tester, for example of the Instron brand (supplied by Instron Corporation). FIG. 6 shows the fastening of nappy pants according to FIG. 3 in the tensile tester for measuring the load to which the tape flap 29 can be subjected without the tape coming away from its attachment to the outer layer of the nappy pants. Only the waist portion 12, on which the tape is permanently arranged, is fastened in the lower clamp 31 of the tensile tester. Only the covering with elastic and not the absorbent element is to be fastened in said lower clamp. The tape flap 29 is pulled out and fastened in the upper clamp 32 of the tensile tester. When pulling starts, the nappy pants are, as can be seen in FIG. 6, to be at right angles to the pulling direction. The maximum value when the tape comes away from the outer layer is recorded. The width of the lower clamp should be at least 200 mm, and the speed of the tensile tester should be 300 mm/min.

For good adhesion to the tape, the outer layer is made from a laminate consisting of, from the outside, at least one layer of spunbond (S), at least one layer of meltblown (M) and, on the inside, a layer of spunbond (S). Non-wovens in the form of laminates of a number of layers of spunbond and meltblown, for example SMS laminate, SMMS laminate etc., can be used as the outer layer on absorbent articles, such as nappies and the like. This type of outer layer can obtain particularly good adhesion of tape of the type used on absorbent disposable articles and at the same time as the laminate is soft and has a textile feel and textile appearance. Such a material is moreover cost-effective compared with other materials with corresponding strength properties.

An example of a suitable outer layer on an absorbent article according to an embodiment of the present invention is an SSMMS laminate from Fibertex with the designation H201010702 with weights per unit area S/S/M/M/S equal to 4.7/4.7/1.5/1.5/4.6 g/m$^2$, that is to say with a total weight per unit area of 17 g/m$^2$.

For reasons of cost and environmental reasons, the tape should have a width which does not exceed 30 mm and preferably does not exceed 20 mm.

The invention is not limited to the illustrative embodiments described above, but a large number of modifications are possible within the scope of the following patent claims.

The tape does not have to be designed as described above but can be folded in a manner other than in a Z-shape before use. The tape flap of the tape can be provided with a stretchable portion to facilitate its extension.

The tape can be designed in many ways so that, when the tape flap has been freed and is extended at right angles to the outer layer, it forms the shape of a T in longitudinal section with the two cross-legs permanently connected to the outer layer and the tape flap constituting the stem portion of said T-shape, as a result of which loads arising in the tape flap are taken up by the two cross-legs.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An absorbent disposable article comprising:
    an inner layer which faces the wearer during use of the article,
    an outer layer,
    an absorbent element arranged between the outer and inner layers, a crotch portion, waist portions located on both sides of the crotch portion which surround the waist of the wearer during use of the article, and a tape permanently attached by a portion on the outside of said outer layer, said tape having a tape flap which is arranged in a parked state during use of the article and which can be brought from its parked state into a state of use in order, after use of the article and after folding or rolling together of the article to form a package, to be usable for closing the package formed, the tape being essentially T-shaped in longitudinal section when the tape flap has been freed from its parked state and raised into an extended state projecting straight out from the outer layer, the tape flap forming a stem portion of said T while two cross-legs of the T constitute the portion that is permanently attached to the outer layer, as a result of which tensile forces in the tape flap are taken up either by the two cross-legs or in the longitudinal direction by one of the cross-legs, the two cross-legs are permanently attached to the outer layer along the whole length of the two cross-legs, the outer layer comprising a laminate of non-woven fabric, the laminate containing at least one outer ply of spunbond non-woven and an inner ply of at least one meltblown non-woven, and the tape being permanently attached to the outer layer with such adhesion that the tape withstands a load of at least 25 N in said tape flap without the tape coming away from the outer layer.

2. The article according to claim 1, wherein the two legs of the tape and the movable tape flap have a width of at most 30 mm.

3. The article according to claim 1, wherein the outer layer comprises an SMS laminate.

4. The article according to claim 1, wherein the outer layer comprises an SMMS laminate.

5. The article according to claim 1, wherein the outer layer comprises an SSMMS laminate.

6. The article according to claim 1, wherein the tape flap in its parked state is folded along a fold line across the tape flap in at least one place along a length of the tape flap in addition to the fold line at a transition to the permanently attached legs of the tape and attached detachably to the legs of the tape by an attachment adhesive of the tape flap.

7. The article according to claim 6, wherein, in addition to said attachment adhesive, which is intended for closing a folded or rolled-together used article, the tape flap has at least one further adhesive area adapted to hold the tape flap detachably in its folded parked state in contact with the legs of the tape.

8. The article according to claim 1, wherein the tape flap has a stretchable portion which makes it possible to lengthen the tape flap when closing a folded-together or rolled-together used article.

9. The article according to claim 1, wherein the tape is attached to the outer layer with such adhesion that the tape flap withstands a load of at least 30 N without the tape coming away from the outer layer.

10. The absorbent article according to claim 1, wherein the absorbent article is nappy pants, a sanitary napkin, or briefs.

11. The absorbent article according to claim 1, wherein the width of two legs of the tape and the movable tape flap is at most 20 mm.

12. The absorbent article according to claim 1, wherein the outer layer consists of an SMS laminate.

13. The absorbent article according to claim 1, wherein the outer layer consists of an SMMS laminate.

14. The absorbent article according to claim 1, wherein the outer layer consists of an SSMMS laminate.

* * * * *